United States Patent [19]
Sabahi

[11] Patent Number: 6,121,500
[45] Date of Patent: Sep. 19, 2000

[54] PRODUCTION OF 6-BROMO-2-NAPHTHOL AND DERIVATIVES

[75] Inventor: Mahmood Sabahi, Baton Rouge, La.

[73] Assignee: Albemarle Corporation, Richmond, Va.

[21] Appl. No.: 09/254,334

[22] PCT Filed: Sep. 13, 1996

[86] PCT No.: PCT/US96/14765

§ 371 Date: Mar. 4, 1999

§ 102(e) Date: Mar. 4, 1999

[87] PCT Pub. No.: WO98/11040

PCT Pub. Date: Mar. 19, 1998

[51] Int. Cl.$^7$ .................................................. C07C 37/02
[52] U.S. Cl. .......................... 568/739; 568/390; 568/393; 568/634; 562/406
[58] Field of Search ..................... 568/739, 647, 568/628, 634, 388, 390, 393; 562/466, 406

[56] References Cited

U.S. PATENT DOCUMENTS

| | | | |
|---|---|---|---|
| 2,576,161 | 11/1951 | Thompson | 260/629 |
| 5,225,603 | 7/1993 | Aslam et al. | 568/315 |
| 5,536,870 | 7/1996 | Wu | 560/56 |

FOREIGN PATENT DOCUMENTS

| | | |
|---|---|---|
| 0179447 | 4/1986 | European Pat. Off. . |
| 380563 | 9/1932 | United Kingdom . |

*Primary Examiner*—Sreeni Padmanabhan
*Attorney, Agent, or Firm*—E. E. Spielman, Jr.

[57] ABSTRACT

A mixture of water and a glycol, such as ethylene glycol, is employed as the solvent for the reaction between 1,6-dibromo-2-naphthol and an alkali metal sulfite in the preparation of 6-bromo-2-naphthol and its derivatives to effect a substantial reduction in reaction time. The glycol/water mol ratio is ordinarily in the range of 0.1–0.5/1, preferably 0.3/0.5/1.

10 Claims, No Drawings

PRODUCTION OF 6-BROMO-2-NAPHTHOL AND DERIVATIVES

This is the U.S. National Stage Application of PCT/US96/14765, filed Sep. 13, 1996.

FIELD OF INVENTION

This invention relates to processes for preparing 6-bromo-2-naphthol and derivatives thereof from 1,6-dibromo-2-naphthol.

BACKGROUND

6-Bromo-2-naphthol is a compound which has particular value as an intermediate in the preparation of non-steroidal antiinflammatory agents, such as 4-(6-methoxy-2-naphthyl)-2-butanone (commonly known as nabumetone) and 2-(6-methoxy-2-naphthyl)-propionic acid (commonly known as naproxen), via 6-bromo-2-methoxynaphthalene.

As disclosed in British Patent 380,563 (I. G. Farbenindustrie), it is known that 6-bromo-2-naphthol can be prepared by the hydrodebromination of 1,6-dibromo-2-naphthol with an alkali metal sulfite in an aqueous or aqueous-alcoholic solvent. This process is commercially unattractive, however, because of its requiring long reaction times to achieve good yields, e.g., 12 hours at reflux temperature to obtain a 99% yield when potassium sulfite is used and 30 hours at reflux temperature to obtain only a 90% yield when sodium sulfite is employed.

It would be desirable to be able to utilize an alkali metal sulfite as the hydrodebrominating agent in the preparation of 6-bromo-2-naphthol and its derivatives without requiring the long reaction times of I. G. Farbenindustrie for the hydrodebromination reaction.

SUMMARY OF INVENTION

It has now been found that the reaction time needed for preparing 6-bromo-2-naphthol by the hydrodebromination of 1,6-dibromo-2-naphthol with an alkali metal sulfite can be reduced by conducting the reaction in a water-glycol mixture as the solvent. Thus, the invention resides in a process which comprises reacting 1,6-dibromo-2-naphthol with an alkali metal sulfite in a water-glycol solvent mixture to prepare 6-bromo-2-naphthol and subsequently, if desired, converting the 6-bromo-2-naphthol product to a 6-bromo-2-alkoxynaphthlene which may then be converted to a pharmaceutically-active derivative, such as nabumetone or naproxen. Embodiments of this invention include:

(1) a process for preparing 6-bromo-2-naphthol by reacting 1,6-dibromo-2-naphthol with an alkali metal sulfite in a water-glycol solvent mixture, (2) a process for preparing a 6-bromo-2-alkoxynaphthalene from 6-bromo-2-naphthol which has been produced by reacting 1,6-dibromo-2-naphthol with an alkali metal sulfite in a water-glycol solvent mixture, and (3) processes for preparing nabumetone or naproxen from a 6-bromo-2-methoxynaphthalene obtained from 6-bromo-2-naphthol which has been produced by reacting 1,6-dibromo-2-naphthol with an alkali metal sulfite in a water-glycol solvent mixture.

DETAILED DESCRIPTION

The alkali metal sulfite which is reacted with 1,6-dibromo-2-naphthol in the practice of the invention may be any suitable alkali metal sulfite but is usually one in which the alkali metal is sodium or potassium, preferably sodium. The amount employed may be any amount in the range of 1–2 mols per mol of 1,6-dibromo-2-naphthol, but optimum results are ordinarily obtained when the sulfite/1,6-dibromo-2-naphthol mol ratio is in the range of 1.4–1.5/1.

Because of cost and availability considerations, ethylene glycol is apt to be preferred as the glycol component of the solvent mixture. However, other glycols (e.g., propylene glycol, butylene glycol, diethylene glycol, and triethylene glycol) are also utilizable. Although economic considerations can make it desirable to minimize the amount of glycol used in conjunction with water to form the solvent mixture, it is important that this amount be large enough to permit good dissolution of the remainder of the reaction mixture. The optimum concentration of glycol in the reaction mixture may vary with the particular glycol employed but can easily be determined by routine experimentation. Ordinarily this amount is such as to provide a glycol/water mol ratio in the range of 0.1–0.5/1, preferably 0.3–0.5/1.

If desired, a base such as potassium carbonate may be used to catalyze the reaction between the sulfite and 1,6-dibromo-2-naphthol, e.g., when the sulfite/1,6-dibromo-2-naphthol mol ratio and/or the glycol/water mol ratio is lower than is normally preferred. However, it is ordinarily found that the utilization of a catalyst is unnecessary.

The novel sulfate/1,6-dibromo-2-naphthol reaction may be conducted at any temperature which permits the reaction to occur but is preferably conducted at reflux temperatures. When reflux temperatures are employed, conversion to 6-bromo-2-naphthol is usually complete in 1–2 hours.

After completion of the sulfite/1,6-dibromo-2-naphthol reaction, the reaction mixture containing the 6-bromo-2-naphthol product can be worked up in any conventional manner to remove impurities and any solvent that the practitioner wishes to separate from the product.

Derivatives of the 6-bromo-2-naphthol product of the foregoing process can be prepared by any processes suitable for preparing those derivatives from 6-bromo-2-naphthol—including both processes conducted in the water-glycol solvent mixture employed in the production of the 6-bromo-2-naphthol and processes conducted in other solvents. Such processes, of course, are already well known. For example:

(1) When it is desired to convert the 6-bromo-2-naphthol to a 6-bromo-2-alkoxynaphthalene, the 6-bromo-2-naphthol may be reacted with an alkylating agent in (a) the water-glycol solvent mixture in which it was synthesized, (b) a solvent mixture obtained by adding a different solvent (e.g., a hydrocarbon, halogenated hydrocarbon, alcohol, or nitrile, such as toluene, ethylene dichloride, isopropyl alcohol, or acetonitrile) to the solution of 6-bromo-2-naphthol in a water-glycol solvent, or (c)—in cases where the 6-bromo-2-naphthol has been isolated from its synthesis mixture—one or more of such different hydrocarbon, halogenated hydrocarbon, alcohol, or nitrile solvents, alone or in admixture with water. The alkylating agent used in this reaction, as is already known, is usually a methylating or ethylating agent, most commonly a methylating agent; and it may be, e.g., dimethyl or diethyl sulfate, methanol or ethanol, or an alkyl halide, such as methyl or ethyl chloride.

(2) When it is wished to convert the 6-bromo-2-naphthol to nabumetone, the 6-bromo-2-naphthol is first converted to a 6-bromo-2-methoxynaphthalene intermediate as described above, and the intermediate is then converted to nabumetone by any of the techniques already known for that conversion. For example, as described in U.S. Pat. No. 5,225,603 (Aslam et al.), the 6-bromo-2-methoxynaphthalene may be (a) reacted with N,N-dimethylformamide to form 6-methoxy-2-naphthaldehyde, which is then condensed with acetone to prepare a 4-(6-methoxy-2-naphthyl)-3-buten-2-one intermediate that is then catalytically hydrogenated to nabumetone or (b) reacted with methyl vinyl ketone to form the 4-(6-methoxy-2-naphthyl)-3-buten-2-one intermediate that is then catalytically hydrogenated to nabumetone.

(3) When it is desired to convert the 6-bromo-2-naphthol to naproxen, the 6-bromo-2-naphthol is first converted to a 6-bromo-2-methoxynaphthalene intermediate as described above, and the intermediate is then converted to naproxen by any of the techniques already known for that conversion. For example, as disclosed in U.S. Pat. No. 5,536,870 (Wu), the 6-bromo-2-methoxynaphthalene may be reacted with ethylene to form 2-methoxy-6-vinylnapthalene, which is then carbonylated to racemic 2-(6-methoxy-2-naphthyl) propionic acid, which can be subsequently resolved to isolate the desired naproxen enantiomer.

Both U.S. Pat. No. 5,225,603 and U.S. Pat. No. 5,536,870 are incorporated herein by reference as if fully set forth.

The invention is advantageous in that its considerably reducing the time required to hydrodebrominate 1,6-dibromo-2-naphthol with an alkali metal sulfite makes it commercially feasible to employ an alkali metal sulfite in preparing 6-bromo-2-naphthol and its derivatives from 1,6-dibromo-2-naphthol.

The following examples are given to illustrate the invention and are not intended as a limitation thereof.

EXAMPLE 1

Charge 15.1 g (0.05 mol) of 1,6-dibromo-2-naphthol (DBN), 8.8 g (0.07 mol) of sodium sulfite, 33.4 g (0.54 mol) of ethylene glycol, and 29.9 g (1.66 mols) of water to a three-necked flask equipped with a condenser, thermometer, and nitrogen inlet. Then heat the reaction mixture at 100–110° C. for 30 minutes. GC analysis shows complete conversion of the DBN starting material.

EXAMPLE 2

Charge the reactor of Example 1 with 7.6 g (0.025 mol) of DBN, 3.5 g (0.028 mol) of sodium sulfite, 55.7 g (0.897 mol) of ethylene glycol, and 29.9 g (1.66 mols) of water, and heat the reaction mixture at 115–116° C. GC analyses show that the use of the lower sodium sulfite/DBN mol ratio gives a slower reaction than the reaction of Example 1—the conversion being 90% after one hour and 92% after two hours.

COMPARATIVE EXAMPLE A

Charge the reactor with 3.0 g (0.01 mol) of DBN, 1.9 g (0.015 mol) of sodium sulfite, 11.3 g (0.075 mol) of triethylene glycol, and 49.9 g (2.77 mols) of water, and heat the reaction mixture at 100° C. With the use of this low glycol/water mol ratio, the conversion is 74% after one hour, 78% after two hours, and 85% after four hours.

COMPARATIVE EXAMPLE B

Charge the reactor with 7.7 g (0.025 mol) of DBN, 3.8 g (0.03 mol) of sodium sulfite, 11.1 g (0.18 mol) of ethylene glycol, and 99.8 g (5.54 mols) of water, and heat the reaction mixture at 100° C. With this use of a low glycol/water mol ratio in combination with a relatively low sulfite/DBN mol ratio, the conversion is only 61% after one hour and increases to only 65% after ten hours.

COMPARATIVE EXAMPLE C

Charge the reactor with 3.0 g (0.01 mol) of DBN, 1.9 g (0.015 mol) of sodium sulfite, 2.0 g (0.015 mol) of potassium carbonate, 0.34 g (0.001 mol) of tetrabutylammonium hydrogen sulfate, 40.5 g (1.26 mols) of methanol, and 49.9 g (2.77 mols) of water, and heat the reaction mixture at reflux. After five hours the conversion is complete, and GC analysis shows 98% 6-bromo-2-naphthol.

COMPARATIVE EXAMPLE D

Essentially repeat Comparative Example C except for using methanol as the only solvent. After three hours at reflux, no reaction has occurred.

COMPARATIVE EXAMPLE E

Essentially repeat Comparative Example C except for not including any methanol in the solvent. After two hours at 100° C., conversion is complete but a second phase appears. GC analysis indicates this second phase to result from the formation of undesired coupled products.

What is claimed is:

1. In a process which comprises reacting 1,6-dibromo-2-naphthol with an alkali metal sulfite to prepare 6-bromo-2-naphthol, the improvement which comprises conducting the reaction in a water-glycol mixture as the solvent.

2. The process of claim 1 wherein the glycol/water mol ratio is in the range of 0.1–0.5/1.

3. The process of claim 2 wherein the glycol/water mol ratio is in the range of 0.3–0.5/1.

4. The process of claim 1 wherein the glycol is ethylene glycol.

5. The process of claim 1 which also comprises alkylating the 6-bromo-2-naphthol to prepare a 6-bromo-2-alkoxynapththalene.

6. The process of claim 1 which also comprises methylating the 6-bromo-2-naphthol to 6-bromo-2-methoxynaphthalene and then converting the 6-bromo-2-methoxynaphthalene thus obtained to 4-(6-methoxy-2-naphthyl)-2-butanone.

7. The process of claim 1 which also comprises methylating the 6-bromo-2-naphthol to 6-bromo-2-methoxynaphthalene and then converting the 6-bromo-2-methoxynaphthalene thus obtained to 2-(6-methoxy-2-naphthyl)propionic acid.

8. In a process for preparing a 6-bromo-2-alkoxynaphthalene by alkylating 6-bromo-2-naphthol, the improvement which comprises employing as the 6-bromo-2-naphthol a product obtained by the 1,6-dibromo-2-naphthol/alkali metal sulfite reaction of claim 1.

9. In a process for preparing 4-(6-methoxy-2-naphthyl)-2-butanone from 6-bromo-2-methoxynaphthalene, the improvement which comprises employing as the 6-bromo-2-methoxynaphthalene a product obtained by methylating a 6-bromo-2-naphthol which has been prepared by the 1,6-dibromo-2-naphthol/alkali metal sulfite reaction of claim 1.

10. In a process for preparing 2-(6-methoxy-2-naphthyl) propionic acid from 6-bromo-2-methoxynaphthalene, the improvement which comprises employing as the 6-bromo-2-methoxynaphthalene a product obtained by methylating a 6-bromo-2-naphthol which has been prepared by the 1,6-dibromo-2-naphthol/alkali metal sulfite reaction of claim 1.

* * * * *